United States Patent [19]

Kojima et al.

[11] 4,220,649
[45] Sep. 2, 1980

[54] 1,4-DIHYDROPYRIDINE-3,5-DICARBOXYLIC ACID ESTER DERIVATIVES

[75] Inventors: Tadao Kojima, Saitama; Toichi Takenaka, Tokyo, both of Japan

[73] Assignee: Yamanouchi Pharmaceutical Co., Ltd., Tokyo, Japan

[21] Appl. No.: 8,085

[22] Filed: Jan. 31, 1979

[30] Foreign Application Priority Data

Feb. 14, 1978 [JP] Japan ................... 53-15673

[51] Int. Cl.$^2$ .................... C07D 213/55; A61K 31/44
[52] U.S. Cl. ..................................... 424/266; 546/281
[58] Field of Search ......................... 546/281; 424/266

[56] References Cited

U.S. PATENT DOCUMENTS 3,996,234  12/1976  Bossert et al. .................. 546/281

Primary Examiner—Alan L. Rotman
Attorney, Agent, or Firm—Burgess, Ryan and Wayne

[57] ABSTRACT

1,4-Dihydropyridine-3,5-dicarboxylic acid ester derivatives shown by the formula

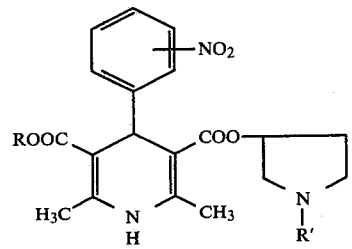

wherein R represents a lower alkyl group and R' represents a hydrogen atom, a lower alkyl group or an aralkyl group, and the therapeutically non-toxic salts thereof.

These compounds possess a vasodilative activity and an antihypertensive activity.

8 Claims, No Drawings

1,4-DIHYDROPYRIDINE-3,5-DICARBOXYLIC ACID ESTER DERIVATIVES

DETAILED DESCRIPTION OF THE INVENTION

This invention relates to 1,4-dihydropyridine-3,5-dicarboxylic acid ester derivatives shown by the general formula

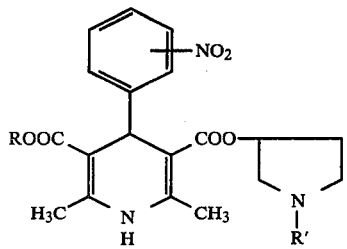

I wherein R represents a lower alkyl group and R' represents a hydrogen atom, a lower alkyl group or an aralkyl group, or the therapeutically non-toxic salts thereof and also the invention further relates to a process of producing these compounds.

As the lower alkyl group in the above formula, there are, for example, methyl group, ethyl group, propyl group, butyl group, isobutyl group, etc., and as the aralkyl group, there are, for example, benzyl group, phenethyl group, etc.

Hitherto, various 1,4-dihydropyridine-3,5-dicarboxylic acid ester derivatives are known and the compound shown by the following formula is practically used for the treatment of angina pectoris;

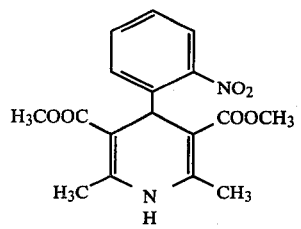

U.S. Pat. No. 3,644,627

Also, as the 1,4-dihydropyridine derivatives wherein the ester moiety is basic, the following compounds are known.

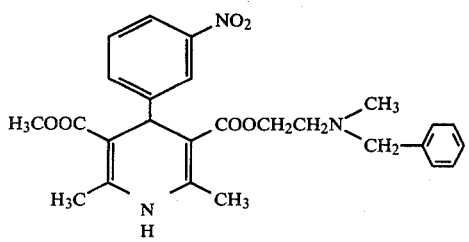

U.S. Pat. No. 3,985,758 and

-continued

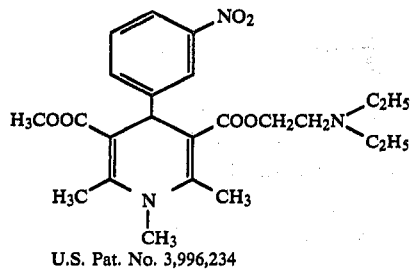

U.S. Pat. No. 3,996,234

In particular, the first compound (U.S. Pat. No. 3,985,758) is now under investigation for use as medicaments.

The compounds of this invention are novel 1,4-dihydropyridine derivatives having different chemical structures from those of the afore-mentioned known 1,4-dihydropyridine derivatives and useful as medicaments.

The compounds of formula I provided by this invention possess a vasodilative activity and an antihypertensitve activity and thus are useful as antihypertensive agents, vasodilators, in particular, coronary vasodilators, and cerebral vascular dilators. Particularly, the characteristics of the compounds of this invention are that they have low toxicity, form easily water-soluble salts thereof, and exhibit a therapeutic effect when administered even in small doses since they are slowly metabolized in vivo.

The compounds of this invention shown by formula I are usually prepared by reacting the acetoacetic acid ester shown by formula II$_1$

II$_1$ wherein R has the same significance as in formula I, with nitrobenzaldehyde shown by formula III

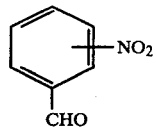

III and the compound shown by formula IV$_1$

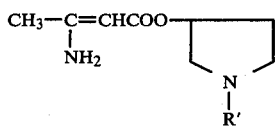

IV$_1$ wherein R' has the same significance as in formula I or by reacting the acetoacetic acid ester shown by formula II$_2$

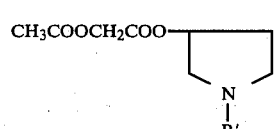

II$_2$ wherein R' has the same significance as in formula I with nitrobenzaldehyde shown by formula III

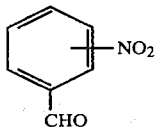

and the compound shown by formula $IV_2$

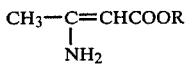

wherein R has the same significance as in formula I.

The reaction for producing the compounds of this invention is performed by mixing the afore-mentioned compound of formula $II_1$ or $II_2$ with an almost equimolar amount of the compound of formula III and an almost equimolar amount of the compound of formula $IV_1$ or $IV_2$ and heating the mixture. In this reaction, a reaction solvent may be or may not be used but when a solvent is used, suitable solvents include alcohols, dioxane, dimethylformamide, dimethylsulfoxide, acetonitrile, water, etc.

In addition, the compound of formula $IV_1$ or $IV_2$ can be obtained by reacting beforehand a compound of formula $II_2$ or $II_1$ with ammonia. A compound of formula $IV_1$ or $IV_2$ thus obtained is reacted, with or without being isolated, with a compound of formula $II_1$ or $II_2$ and a compound of formula III to provide the desired compound of formula I.

Furthermore, the compounds of the following formula obtained by reacting beforehand the compound of $II_1$ or $II_2$ with the compound of formula III

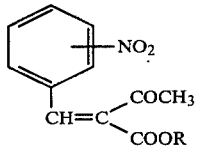 or

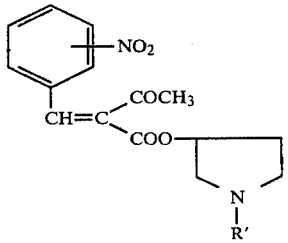

can also provide the desired compounds of formula I by reacting, with or without being isolated, with the compound of formula $IV_1$ or $IV_2$.

The desired compounds of this invention shown by formula I obtained in any of the afore-mentioned processes can be isolated and purified by conventional methods such as column chromatography, etc.

The compounds of general formula I can be desirably converted into the therapeutically non-toxic salts thereof, for example, mineral acid salts such as hydrochlorides, sulfates, phosphates, etc., or organic acid salts such as acetates, fumarates, maleates, tartarates, etc.

The salts of the compounds of formula I are suitable for liquid pharmaceutical preparations (especially injection) since these salts are highly soluble in water without using solubilizing agents.

The appropriate dose of the compound of this invention for human beings is 0.1–1.0 mg per single dose in intravenous administration and 5–20 mg per single dose in oral administration, two or three times a day being appropriate.

The excellent antihypertensive activity of the compounds of this invention is proved by the following tests in the comparison with a 1,4-dihydropyridine derivative having a basic ester moiety, 2,6-dimethyl-4-(3'-nitrophenyl)-1,4-dihydropyridine-3,5-dicarboxylic acid 3-methyl ester-5-β-(N-benzyl-N-methylamino)ethyl ester hydrochloride (Compound B, U.S. Pat. No. 3,985,758):

(I) Procedures:

Male, conscious spontaneously hypertensive rats, Okamoto and Aoki strain were used in the study. Systolic blood pressure and heart rate were determined by tail plethysmographic methods employing a Narco electrosphygmomanometer (PE-300). The drug suspended in 0.5% methyl cellulose were administered orally in a dosage volume of 5 ml/Kg.

(II) Results and conclusion:

As shown in Table 1, the compound of this invention caused hypotensive activity about 5 times more potent than Compound B when orally administered to spontaneously hypertensive rats. These results indicate that hypotensive effect of the compound of this invention was more potent than that of Compound B by oral administration. Since the anti-hypertensive agent was usually administered by oral route, these results may prove that the compound of this invention is suitable for treatment of hypertensive subjects.

Table 1

Effects on systolic blood pressure and heart rate in conscious spontaneously hypertensive rat.

| Compound | Dose mg/kg p.o. | No. of animals | Parameters | Initial value | Changes in systolic blood pressure (ΔmmHg) and heart rate (Δbeats/min) at stated time (hr) | | | |
|---|---|---|---|---|---|---|---|---|
| | | | | | 1 | 2 | 4 | 6 |
| Compound B (known compound) | 10 | 10 | Blood pressure | 196 ± 11.8 | −41 ± 6.7 | −39 ± 8.3 | −28 ± 7.8 | −25 ± 8.2 |
| | | | Heart rate | 380 ± 12.5 | 21 ± 31.4 | 36 ± 27.5 | −9 ± 22.7 | −27 ± 20.6 |
| | 30 | 10 | Blood pressure | 190 ± 12.1 | −82 ± 11.7 | −71 ± 18.9 | −78 ± 16.1 | −62 ± 17.0 |
| | | | Heart rate | 363 ± 17.5 | 93 ± 18.4 | 63 ± 22.7 | 41 ± 25.9 | −8 ± 22.7 |
| Compound A (hydrochloride of compound of Ex. 1) | 3 | 10 | Blood pressure | 213 ± 16.8 | −61 ± 14.6 | −49 ±0 11.7 | −34 ± 8.3 | −43 ± 11.4 |
| | | | Heart rate | 388 ± 12.6 | 23 ± 21.9 | 9 ± 15.5 | −22 ± 21.4 | −22 ± 19.2 |
| | 10 | 9 | Blood pressure | 204 ± 17.3 | −99 ± 14.8 | −83 ± 13.3 | −79 ± 15.1 | −81 ± 15.7 |
| | | | Heart rate | 377 ± 16.8 | 68 ± 12.9 | 60 ± 13.0 | 37 ± 17.4 | − ± 15.7 |

The process for producing the desired compounds of this invention is illustrated by the following examples.

EXAMPLE 1

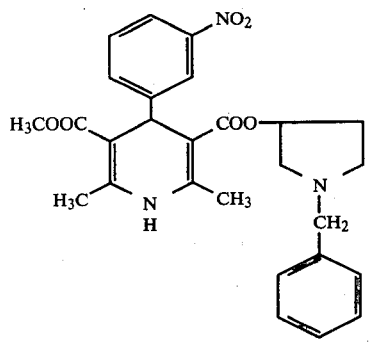

In 5 ml of isopropyl alcohol were dissolved 1.5 g (0.01 mole) of 3-nitrobenzaldehyde, 2.6 g (0.01 mole) of 1-benzyl-3-acetoacetyloxypyrrolidine, and 1.3 g (0.01 mole) of β-aminocrotonic acid methyl ester and then the solution was refluxed for 8 hours. The solvent was distilled off under reduced pressure, the residue obtained was dissolved in a small amount of chloroform, and the solution was applied to silica gel column chromatography (column diameter 1.5 cm, height 20 cm, and about 200 ml of chloroform was used as the eluant). The eluates were collected and concentrated to give 3.4 g of oily 2,6-dimethyl-4-(3'-nitrophenyl)-1,4-dihydropyridine-3,5-dicarboxylic acid-3-(1-benzylpyrrolidin-3-yl)ester-5-methyl ester.

Elemental analysis for $C_{27}H_{29}N_3O_6$:

|  | C | H | N |
|---|---|---|---|
| Calculated: | 65.98% | 5.95% | 8.55% |
| Found: | 65.69% | 5.83% | 8.47% |

Nuclear magnetic resonance spectra (CDCl₃):

| δ: | 1.24–3.0 | (pyrrolidine ring Hs, m, 6H) |
|---|---|---|
| | 2.33 | (H₃C–, CH₃, s, 6H) |
| | 3.60 | (N–CH₂–, q, 2H) |
| | 3.64 | (CH₃—COO—, s, 3H) |
| | 5.09 | (dihydropyridine H and pyrrolidine H, s, m, 2H) |
| | 6.46 | (dihydropyridine NH, s, 1H) |
| | 7.28 | (nitrophenyl and phenyl Hs, m, 6H) |
| | 7.64 | (nitrophenyl H, m, 1H) |
| | 8.0 | (nitrophenyl H, double d, 1H) |
| | 8.12 | (nitrophenyl H, d, 1H) |

In addition, 1-benzyl-3-acetoacetyloxypyrrolidine used in this example was prepared by the following manner.

That is, to 8.8 g (0.05 mole) of 1-benzyl-3-hydroxypyrrolidine was added a catalytic amount (0.1 g) of sodium acetate and after stirring the mixture well, 5.0 g (0.06 mole) of diketene was gradually added dropwise to the mixture. Thereafter, the resultant mixture was stirred at 80° C. for 3 hours. After cooling the reaction mixture, it was distilled under reduced pressure to provide 10.3 g of product having a boiling point of 130°–135° C./0.1 mmHg.

Elemental analysis for $C_{15}H_{19}NO_3$:

|  | C | H | N |
|---|---|---|---|
| Calculated: | 68.94% | 7.33% | 5.36% |
| Found: | 68.81% | 7.20% | 5.05% |

Nuclear magnetic resonance spectra (CDCl₃):

| δ: | 1.6–3.0 | (pyrrolidine ring Hs, m, 6H) |
|---|---|---|
| | 2.2 | (CH₃—COO—, s, 3H) |
| | 3.38 | (—COCH₂—COO—, s, 2H) |
| | 3.60 | (N–CH₂–, q, 2H) |
| | 5.22 | (—COO–CH, m, 1H) |

-continued 7.6 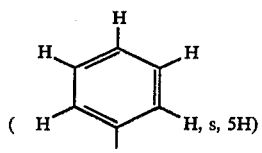
( H, s, 5H)

EXAMPLE 2

A sterile aqueous solution for injection, containing in 1 ml. 1 mg. of 2,6-dimethyl-4-(3'-nitrophenyl)-1,4-dihydropyridine-3,5-dicarboxylic acid-3-(1-benzylpyrrolidin-3-yl) ester-5-methyl ester hydrochloride (Compound A) was prepared from the following formulation.

Compound A: 100 mg.

Glucose: 5000 mg.

Water for injection up to 100 ml.

Compound A was dissolved in about 80 ml. of water, then the resultant solution was filled up to 100 ml. by the addition of water and sterilized by filtration. The sterile solution was filled in 100 light intercepting ampoules and the ampoules sealed.

EXAMPLE 3

A tablet containing in 1 tablet 10 mg. of 2,6-dimethyl-4-(3'-nitrophenyl)-1,4-dihydropyridine-3,5-dicarboxylic acid-3-(1-benzylpyrrolidin-3-yl) ester-5-methyl ester hydrochloride (Compound A) was prepared from the following formulation.

Compound A: 10 g.

Lactose: 80 g.

Starch: 29 g.

Magnesium Stearate: 1 g.

What is claimed is:

1. 1,4-Dihydropyridine-3,5-dicarboxylic acid ester derivatives represented by the formula

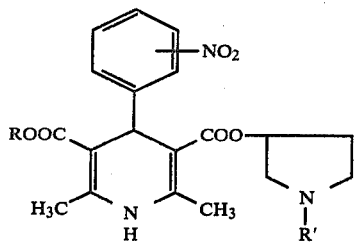

wherein R represents a lower alkyl group and R' represents a hydrogen atom, a lower alkyl group, or benzyl phenylethyl, and the therapeutically non-toxic salts thereof.

2. 2,6-Dimethyl-4-(3'-nitrophenyl)-1,4-dihydropyridine-3,5-dicarboxylic acid-3-(1-benzylpyrrolidin-3-yl)ester 5-methyl ester or the hydrochloride thereof as claimed in claim 1.

3. A compound as claimed in claim 1, wherein said salts are selected from the group consisting of the hydrochloride, sulfate, phosphate, acetate, fumarate, maleate, and tartrate.

4. An antihypertensive composition comprising a mixture of a 1,4-Dihydropyridine-3,5-dicarboxylic acid ester derivative represented by the formula

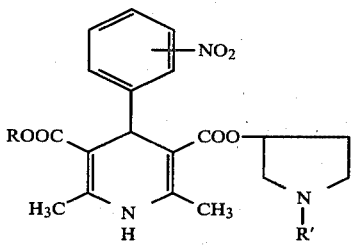

wherein R represents a lower alkyl group and R' represents a hydrogen atom, a lower alkyl group, benzyl or phenylethyl, or a therapeutically non-toxic salt thereof as the active ingredient, and a therapeutically acceptable carrier therefor.

5. A composition as claimed in claim 4, comprising 2,6-Dimethyl-4-(3'nitrophenyl)-1,4-dihydropyridine-3,5-dicarboxylic acid-3-(1-benzylpyrrolidin-3-yl)ester 5-methyl ester or the hydrochloride thereof as the active ingredient.

6. A method of treating hypertension comprising administering an antihypertensive effective amount of the composition of claim 4 or 5.

7. A method as claimed in claim 6, comprising administering by intravenous injection an amount of said composition to provide from 0.1 to 1 mg of said active ingredient per dose in an aqueous solution.

8. A method as claimed in claim 6, comprising orally administering an amount of said composition to provide from 5 to 20 mg of said active ingredient per dose.

* * * * *